United States Patent [19]

Hall et al.

[11] Patent Number: 5,298,663
[45] Date of Patent: Mar. 29, 1994

[54] PROCESS FOR THE PREPARATION OF PROTECTED PHOSPHINE OXIDES

[75] Inventors: Roger G. Hall, Aesch; Peter Riebli, Buckten, both of Switzerland

[73] Assignee: Ciba-Geigy Corporation, Ardsley, N.Y.

[21] Appl. No.: 35,524

[22] Filed: Mar. 23, 1993

Related U.S. Application Data

[63] Continuation of Ser. No. 840,353, Feb. 24, 1992, abandoned.

[30] Foreign Application Priority Data

Feb. 27, 1991 [GB] United Kingdom ............... 9104050

[51] Int. Cl.$^5$ ............................................. C07F 9/53
[52] U.S. Cl. ............................. 568/14; 568/15; 556/405
[58] Field of Search ............... 568/14, 15; 556/405

[56] References Cited

U.S. PATENT DOCUMENTS

| | | | |
|---|---|---|---|
| 4,339,443 | 7/1982 | Baillie et al. | 424/200 |
| 4,473,710 | 9/1984 | Gautier et al. | 568/15 |
| 4,933,478 | 6/1990 | Wardleworth et al. | 558/104 |

FOREIGN PATENT DOCUMENTS

| | | | |
|---|---|---|---|
| 0307362 | 3/1989 | European Pat. Off. | |
| 0351548 | 1/1990 | European Pat. Off. | 568/14 |
| 0923532 | 12/1960 | United Kingdom | 568/14 |

OTHER PUBLICATIONS

S. A. Buckler et al., Tetrahedron 18, 1211 (1962).
T. L. Emmick et al., J. Am. Chem. Soc., 90, 3459 (1968).
R. L. Wife et al., Synthesis 1983, 71–73, "Phosphine oxide anions in the Synthesis of Phosphine Ligands".
M. J. Gallagher et al., Aust. J. Chem. 33, 287 (1980).
Derwent Abst. 91-052929/08, 1991.
T. A. M. Van Schaik et al., Tetrahedron Letters 24, 1303 (1983).
Chem. Absts. 113, 52233z (1990).

*Primary Examiner*—Marianne M. Cintins
*Assistant Examiner*—Margaret J. Page
*Attorney, Agent, or Firm*—Luther A. R. Hall

[57] ABSTRACT

A process for the preparation of a protected phosphine oxide which comprises reacting a phosphinate ester having a protecting group on the phosphorus atom with an organomagnesium halide or an organolithium compound at a temperature of $-70°$ C. to $65°$ C. Protected phosphine oxides so prepared are useful intermediates for the preparation of tertiary phosphine oxides and acylphosphine oxide photoinitiators.

13 Claims, No Drawings

PROCESS FOR THE PREPARATION OF PROTECTED PHOSPHINE OXIDES

This application is a continuation, of application Ser. No. 07/840,353, filed Feb. 24, 1992 now abandoned.

This invention relates to the preparation of protected phosphine oxides, and their use as intermediates.

Phosphine oxides, particularly tertiary phosphine oxides, are useful compounds in themselves, for example in metal extraction processes, as catalysts for the reaction of isocyanates with alkylene oxides or cyclic carbonate esters, or in biological applications such as plant protection. Acyl phosphine oxides are useful as photoinitiators for the photopolymerisation of unsaturated materials. Phosphine oxides are also important intermediates for the production of other organophosphorus compounds such as phosphines and phosphonium salts, which are used, particularly as catalysts, in a wide variety of industrial processes.

It is known, for example from S. Buckler and M. Epstein, Tetrahedron 18, 1211 (1962), that primary phosphine oxides are unstable compounds which are not isolated in pure form. Secondary phosphine oxides have been prepared by reacting a phosphinate ester with a Grignard reagent as described by T. L. Emmick and R. L. Letsinger, J. Amer. Chem. Soc. 90, 3459 (1968) or by reacting a phosphinate ester with an alkoxyphenyllithium as described by R. L. Wife et al, Synthesis 1983, 71.

It has now been found that primary and secondary phosphine oxides having a protected P—H bond can be prepared by reaction of a protected phosphinate ester with an organomagnesium halide or an organolithium compound. These oxides, which can be isolated as stable compounds, many of which are novel, are useful intermediates. They permit the controlled sequential introduction of different substituents on a phosphorus atom to give unsymmetrical phosphine oxides which are not readily obtainable by other routes.

Accordingly, the present invention provides a process for the preparation of a protected phosphine oxide which comprises reacting a phosphinate ester having a protecting group on the phosphorus atom with an organomagnesium halide or an organolithium compound at a temperature of −70° C. to 65° C.

The protected phosphinate ester may be a $C_1$–$C_{20}$ alkyl ester of phosphinic acid in which one of the hydrogen atoms attached to phosphorus is replaced by a protecting group. It is generally of formula

    I where $R^1$ denotes a $C_1$–$C_4$ alkyl group and Q denotes a protecting group.

Suitable protecting groups Q include those known to be effective in protecting P—H bonds, such as those described in EP 0009348, Aust. J. Chem. 33, 292 (1980) and U.S. Pat. No. 4,933,478. Preferably, Q is of formula

    II where $R^2$ denotes a hydrogen atom or a $C_1$–$C_4$ alkyl group and $R^3$ and $R^4$ each independently denote a $C_1$–$C_4$ alkyl group.

$R^1$, $R^2$, $R^3$ and $R^4$ as $C_1$–$C_4$ alkyl may denote methyl, ethyl, n-propyl, isopropyl, n-butyl, isobutyl or tert.butyl. Preferably, $R^2$ denotes hydrogen, methyl or ethyl, especially hydrogen or methyl, and $R^1$, $R^3$ and $R^4$ are the same and each denote methyl or ethyl, especially ethyl.

The organomagnesium halide is generally of formula $$R^5MgX \qquad \text{III}$$

where $R^5$ denotes a monovalent organic group which is a $C_1$–$C_{20}$ aliphatic group, a $C_3$–$C_{12}$ cycloaliphatic group, a $C_6$–$C_{15}$ aromatic group or a $C_7$–$C_{16}$ araliphatic group, and X denotes a chlorine, bromine or iodine atom.

The organolithium compound is generally of formula $$R^5Li \qquad \text{IV}$$

where $R^5$ is as hereinbefore defined.

$R^5$ may denote a $C_1$–$C_{20}$ alkyl group, a $C_2$–$C_{20}$ alkenyl group, a $C_3$–$C_{12}$ cycloalkyl group, a $C_6$–$C_{15}$ aryl group optionally substituted by halogen, or a $C_7$–$C_{16}$ aralkyl group.

$R^5$ as $C_1$ to $C_{20}$ alkyl may denote methyl, ethyl, n-propyl, isopropyl, n-butyl, isobutyl, tert. butyl, n-pentyl, n-hexyl, n-octyl, 2-ethylhexyl, decyl, dodecyl, pentadecyl, hexadecyl, octadecyl or eicosyl.

$R^5$ as $C_2$ to $C_{20}$ alkenyl may denote vinyl, allyl, butenyl, pentenyl, hexenyl, octenyl, decenyl, dodecenyl, pentadecenyl, hexadecenyl, octadecenyl or eicosenyl.

$R^5$ as $C_3$ to $C_{12}$ cycloalkyl may denote cyclopropyl, cyclopentyl, methylcyclopentyl, cyclohexyl, 4-methylcyclohexyl, cycloheptyl, cyclooctyl, cyclodecyl or cyclododecyl.

$R^5$ as optionally substituted $C_6$ to $C_{15}$ aryl may denote phenyl, o-tolyl, m-tolyl, p-tolyl, o-xylyl, m-xylyl, p-xylyl, alpha-naphthyl, beta-naphthyl, 1-anthryl or 2-anthryl, any of which groups may be substituted by one or two halogen, especially chlorine, atoms. $R^5$ as $C_7$ to $C_{16}$ aralkyl may denote benzyl, 4-methylbenzyl, 2-phenylethyl, 2-phenylpropyl, 3-phenylpropyl or diphenylmethyl.

Preferred embodiments of the invention include those where $R^5$ denotes a $C_1$ to $C_{18}$ alkyl group; a $C_2$–$C_{12}$ alkenyl group; a $C_3$ to $C_8$ cycloalkyl group; a $C_6$ to $C_{10}$ aryl group, optionally substituted by halogen; or a $C_7$ to $C_{11}$ aralkyl group. More preferably $R^5$ denotes a $C_1$ to $C_{18}$ alkyl group; a $C_2$–$C_8$ alkenyl group; a $C_3$, $C_5$ or $C_6$ cycloalkyl group; a $C_6$ to $C_8$ aryl group, optionally substituted by one or two chlorine atom; or a $C_7$ to $C_9$ aralkyl group. Especially preferred groups $R^5$ are methyl, ethyl, n-butyl, tert.butyl, octadecyl, allyl, cyclohexyl, phenyl, p-chlorophenyl or benzyl.

Reaction of the protected phosphinate ester with the organomagnesium halide or the organolithium compound is usually carried out under an inert atmosphere; it may be effected at superatmospheric pressure or, preferably, at atmospheric pressure. The organomagnesium halide or organolithium compound is generally used in a stoichiometric excess, more usually in an amount of at least 2 mols per mol of the phosphinate ester. However, with certain reactants of formula III or IV, for example those where $R^5$ denotes an allyl group, it is preferred to use the reactant of formula III or IV in an amount of 1 mol or less per mol of the phosphinate ester.

Reaction of the phosphinate ester with the organomagnesium halide is preferably effected at a temperature of 0° to 25° C. Reaction of the phosphinate ester with the organolithium compound is preferably conducted at −50° to 25° C. Both reactions are conveniently carried out in a non-protic solvent such as diethyl ether or tetrahydrofuran.

Phosphinate esters having a protecting group on the phosphorus atom, such as those of formula I, are either known or may be prepared by known methods, for example as described in EP 0009348, Aust. J. Chem. 33, 292 (1980) or U.S. Pat. No. 4,933,478. Organomagnesium halides such as those of formula III and organolithium compounds such as those of formula IV are readily available or may be prepared by known methods.

Reaction of a protected phosphinate ester of formula I with an organomagnesium halide of formula III or an organolithium compound of formula IV gives a protected primary phosphine oxide of formula

   V where $R^5$ and Q are as hereinbefore defined.

The protected primary phosphine oxide obtained by reaction of the phosphinate with the magnesium or lithium compound, e.g. that of formula V, may be converted into a protected secondary phosphine oxide by reaction with a compound of formula $R^6Z$   VI where $R^6$ denotes a monovalent organic group which is a $C_1$–$C_{20}$ aliphatic group, a $C_3$–$C_{12}$ cycloaliphatic group, a $C_6$–$C_{15}$ aromatic group or a $C_7$–$C_{16}$ araliphatic group and Z denotes a leaving atom or group.

$R^6$ may denote a $C_1$–$C_{20}$ alkyl group, a $C_2$–$C_{20}$ alkenyl group, a $C_3$–$C_{12}$ cycloalkyl group, a $C_6$–$C_{15}$ aryl group optionally substituted by halogen, or a $C_7$–$C_{16}$ aralkyl group. It may be chosen from the alkyl, alkenyl, cycloalkyl, aryl and aralkyl groups hereinbefore mentioned as examples of $R^5$. $R^5$ and $R^6$ may be the same or different. Preferably $R^6$ denotes a $C_1$–$C_4$ alkyl group or a $C_7$ to $C_9$ aralkyl group, especially methyl, n-propyl, isobutyl or benzyl.

The leaving atom or group Z in formula VI may be, for example, a halogen atom or a residue of an organic acid after removal of an acidic hydrogen atom therefrom, such as an organic sulphonate group, e.g. a p-toluenesulphonate or trifluoromethanesulphonate group. Preferably Z is a halogen atom or an arylsulphonate group, especially a bromine atom or a p-toluenesulphonate group. Thus compounds of formula VI are known or may be prepared by known methods, preferred compounds including $C_1$–$C_4$ alkyl halides, $C_7$–$C_9$ aralkyl halides, $C_1$–$C_4$ alkyl esters of arylsulphonic acids and $C_7$–$C_9$ aralkyl esters of arylsulphonic acids.

Especially preferred compounds of formula VI are isobutyl bromide and benzyl bromide.

The reaction between the protected primary phosphine oxide and $R^6Z$ may be carried out under conditions conventional for substitution reactions at a P—H bond, for example using a base such as sodium, sodium hydride or an alkyllithium in an inert organic solvent such as tetrahydrofuran.

The protected primary phosphine oxide of formula V may alternatively be converted into a protected secondary phosphine oxide by reacting it with a silylating agent of formula $(R^7)_3SiX$   VII where each $R^7$ independently denotes a $C_1$–$C_6$ alkyl group and X is a chlorine, bromine or iodine atom, in the presence of a tertiary base, to give a silyl compound of formula

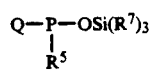   VIII and reacting this silyl compound with a compound of formula VI as hereinbefore described.

The reaction of the compound of formula V with a silylating agent of formula VII, for example dimethyltert.butyl silyl chloride, dimethyl(2,3-dimethyl-2-butyl) silyl chloride or, preferably, trimethylsilyl chloride or triethylsilyl chloride, to give a compound of formula VIII is carried out in the presence of a tertiary base such as pyridine or triethylamine. The reaction conditions vary according to the silylating agent used. The reaction temperature may range from −20° C. to 150° C. and the reaction may be effected with or without the use of an inert solvent such as diethylether, toluene, tetrahydrofuran or dioxan. Alternatively an excess of the silylating agent may be used as diluent. While the molar ratio of silylating agent to compound of formula V is conveniently 1:1, molar excess amounts of silylating agent may be used to advantage in certain cases.

The compound of formula VIII is then reacted with a compound of formula VI, for example one of those hereinbefore described, to give a protected secondary phosphine oxide. This reaction may be carried out under conditions conventional for substitution reactions on P (III) species. For example, when Z is a halogen such as chloro or bromo, the reaction is preferably carried out by the Arbuzov method, e.g. at temperatures between ambient and elevated temperatures, such as 160° C., while removing the trialkylsilyl halide formed in the reaction.

Conversion of protected primary phosphine oxides of formula V into protected secondary phosphine oxides as hereinbefore described gives protected secondary phosphine oxides of formula

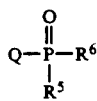   IX where $R^5$, $R^6$ and Q are as hereinbefore described.

Many of the protected phosphine oxides of formulae V and IX are novel compounds. Accordingly, the present invention also provides protected phosphine oxides of formula

where Q is as hereinbefore defined, R$^8$ denotes a hydrogen atom or R$^6$, and R$^5$ and R$^6$ each independently denote a C$_1$–C$_{20}$ alkyl group, a C$_2$–C$_{20}$ alkenyl group, a C$_3$–C$_{12}$ cycloalkyl group, a C$_6$–C$_{15}$ aryl group optionally substituted by halogen, or a C$_7$–C$_{16}$ aralkyl group, as hereinbefore described, provided that R$^5$ and R$^6$ are not both phenyl when Q is a dimethoxymethyl or diethoxymethyl group.

Subject to the above proviso, preferred compounds of formula X are those where R$^5$ and Q have the preferred meanings hereinbefore described and R$^8$ denotes a hydrogen atom or R$^6$ having the preferred meaning hereinbefore described.

Especially preferred compounds of formula X are those where Q denotes a group of formula II, R$^8$ denotes hydrogen, R$^2$ denotes hydrogen, R$^3$ and R$^4$ each denote ethyl, and R$^5$ denotes methyl, ethyl, n-butyl, tert.butyl, octadecyl, allyl, cyclohexyl, phenyl, p-chlorphenyl or benzyl; those where R$^5$ denotes methyl, R$^8$ denotes hydrogen, R$^2$ denotes methyl and R$^3$ and R$^4$ each denote ethyl; those where R$^5$ denotes n-butyl or tert.butyl, R$^2$ denotes hydrogen, R$^3$ and R$^4$ each denote ethyl and R$^8$ denotes isobutyl or benzyl; those where R$^5$ denotes phenyl, R$^2$ denotes hydrogen, R$^3$ and R$^4$ each denote ethyl and R$^8$ denotes n-propyl or methyl; and that were R$^8$ denotes methyl, R$^5$ denotes methyl, R$^2$ denotes hydrogen and R$^3$ and R$^4$ each denote ethyl.

The protecting group in the protected phosphine oxides, e.g. the Q in compounds of formula X, may be removed to generate unprotected phosphine oxides having reactive P—H groups by means of known cleaving reactions. Thus it may be removed by treatment with an acid under hydrolytic conditions, preferably with a mineral acid, e.g. a hydrohalic acid such as hydrochloric acid in dilute or concentrated aqueous form. Another known method of cleaving the protecting group comprises treating the compound of formula X with an organic silyl halide such as trimethylsilyl bromide or trimethylsilyl iodide followed by hydrolysis; the reaction is preferably conducted at elevated temperature, e.g. while refluxing the reaction mixture and, if necessary, using an organic diluent, in a closed vessel or under an atmosphere of an inert gas.

The secondary phosphine oxide obtained by removing the protecting group from compounds of formula X where one of R$^5$ and R$^8$ denotes tert.butyl and the other denotes benzyl, i.e. tert.butyl (benzyl) phosphine oxide, is believed to be novel.

The protected phosphine oxides prepared in accordance with the invention are useful as intermediates for the preparation of other organophosphorus compounds. The protecting group may be removed in situ and the resulting phosphine oxide subjected to various reactions. For example, secondary phosphine oxides generated in situ from compounds of formula X may be reacted via the corresponding P(III) species with an acyl halide to give acyl phosphine oxides for use as photoinitiators for the photopolymerisation of ethylenically unsaturated materials such as acrylates.

For example, secondary phosphine oxides generated from compounds of formula IX may be reacted with a silylating agent of formula VII in the presence of a tertiary base to give a P(III) silyl compound of formula

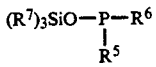

where R$^5$, R$^6$ and R$^7$ are as hereinbefore defined, and reacting this silyl compound with an acyl halide to give an acylphosphine oxide photoinitiator, for example an acylphosphine oxide photoinitiator as described in EP 0 413 657.

The reaction of the secondary phosphine oxide with the silylating agent of formula VII is analogous to the reaction of the latter with the phosphine oxide of formula V hereinbefore described and may be carried out under similar conditions. Reaction of the P(III) compound of formula XI with the acyl halide may be carried out under conventional acylation conditions. Conversion of the secondary phosphine oxide into the acyl phosphine oxide may be carried out without isolation of the P(III) species of formula XI, as described in EP 0 413 657. Suitable acyl halides include benzoyl halides, particularly halogen-, alkyl- or alkoxy-substituted benzoyl halides, as described in EP 0 413 657.

Using the procedure hereinbefore described, secondary phosphine oxides such as methyl(benzyl)phosphine oxide, butyl(benzyl)phosphine oxide, octyl(benzyl)phosphine oxide, cyclohexyl(benzyl)phosphine oxide, dibenzyl phosphine oxide, bis(2-phenylethyl)phosphine oxide, diphenylphosphine oxide, dibutylphosphine oxide or bis(cyclohexyl)phosphine oxide may be reacted, via the corresponding silylated P(III) species, with benzoyl halides such as 2,6-dichlorobenzoyl chloride, 2,6-dimethoxybenzoyl chloride or 2,4,6-trimethylbenzoyl chloride to give acylphosphine oxide photoinitiators suitable for use in photopolymerisation of acrylates. In especially preferred reactions, n-butyl(benzyl) phosphine oxide, generated from n-butyl(benzyl)(diethoxymethyl)phosphine oxide as hereinbefore described, is reacted with 2,6-dimethoxybenzoyl chloride or 2,4,6-trimethylbenzoyl chloride to give photoinitiators which can effect rapid polymerisation of acrylates.

Protected primary phosphine oxides of formula V are usually converted into protected secondary phosphine oxides as hereinbefore described before subjection to other reactions. Secondary phosphine oxides generated from protected secondary oxides of formula IX can be reacted with a compound of formula VI as hereinbefore defined to give a tertiary phosphine oxide, for example a tertiary oxide not readily available by other routes, which can in turn be reduced using known procedures to a tertiary phosphine for use as catalysts or conversion into phosphonium salts for use as catalysts.

The invention is illustrated by the following Examples.

EXAMPLE 1

A 3 molar solution of methylmagnesium chloride in tetrahydrofuran (34.0 ml) is placed in a dry flask under an atmosphere of argon and cooled to 0°–5° C. by means of an ice-bath. To this solution is added 10.0 g of ethyl diethoxymethyl phosphinate. The rate of addition is adjusted to maintain an internal temperature below 20° C. After the addition is complete, the mixture is stirred at room temperature for 2 hours and re-cooled to 0°–5° C. To the mixture is then added a solution of 14.1 g potassium carbonate in 15 ml of water to precipitate inorganic salts, the rate of addition being adjusted to maintain an internal temperature below 15° C. When addition is complete, the inorganic salts are removed by filtration, washed three times with ethanol and the filtrate is evaporated under reduced pressure to remove the solvents. The crude product obtained is purified by chromatography on silica using as eluent a mixture, by volume, of 10 parts ethyl acetate and 1 part ethanol. There is obtained methyl(diethoxymethyl) phosphine oxide as a colourless oil.

$^{31}P$ NMR 26.6 ppm (CDCl$_3$) J$_{P-H}$=468.6 Hz $^1H$ NMR δ1.3(t, J=9 Hz, 6H); δ1.6(d.d, J=20 Hz, J=5.4 Hz, 3H); δ3.8(m, 4H); δ4.3(m, 0.5H); δ4.9(d.d, J=12.5 Hz, J=1.8 Hz, 1H); δ9.6(m, 0.5H)

EXAMPLE 2

By a procedure analogous to that of Example 1, but using 5.0 g of ethyldiethoxymethyl phosphinate and 51.0 ml of a molar solution of 4-chlorophenylmagnesium bromide in diethyl ether and adding 7.05 g of potassium carbonate in 10 ml of water to precipitate inorganic salts, 4-chlorophenyl (diethoxymethyl) phosphine oxide is obtained as a colourless oil.

$^{31}P$ NMR 21.7 ppm (CDCl$_3$) J$_{P-H}$=484.4 Hz $^1H$ NMR δ1.3(m, 6H); δ3.9(m, 4H); δ4.8(m, 0.5H); δ5.0(d.d, J=9 Hz, J=1.5 Hz, 1H); δ7.8(m, 4H); δ10.2(m, 0.5H)

EXAMPLE 3

By a procedure analogous to that of Example 1, but using 60.0 g of ethyldiethoxymethyl phosphinate and 204 ml of a 3 molar solution of phenylmagnesium bromide in diethyl ether and adding 84.6 g of potassium carbonate in 100 ml of water to precipitate inorganic salts, phenyl (diethoxymethyl) phosphine oxide is obtained as a colourless oil.

$^{31}P$ NMR 23.3 ppm (CDCl$_3$) J$_{P-H}$=480.0 Hz

EXAMPLE 4

Following a procedure analogous to that of Example 1, but using 1.96 g of ethyldiethoxymethyl phosphinate and 20 ml of a molar solution of octadecylmagnesium chloride in tetrahydrofuran and adding 4.14 g of potassium carbonate in 5 ml of water to precipitate inorganic salts, octadecyl(diethoxymethyl) phosphine oxide is obtained as a white waxy solid, m.p. 54°-8° C.

$^{31}P$ NMR 32.6 ppm (CDCl$_3$) J$_{P-H}$=447.5 Hz $^1H$ NMR δ2.0–0.8(m, 43H); δ3.9(q, J=8.7 Hz, 4H); δ4.1(m, 0.5H, δ4.9(d, J=10 Hz, 1H); δ9.5(m, 0.5H)

EXAMPLE 5

By a procedure analogous to that of Example 1, but using 1.96 g of ethyl diethoxymethylphosphinate and 20 ml of a molar solution of benzylmagnesium chloride in diethyl ether and adding 4.14 g of potassium carbonate in 5 ml of water to precipitate inorganic salts, benzyl (diethoxymethyl) phosphine oxide is obtained as a colourless oil.

$^{31}P$ NMR 31.7 ppm (CDCl$_3$) J$_{P-H}$=461.5 Hz $^1H$ NMR δ1.3(t, J=9 Hz, 6H); δ3.5(d.d, J=14.5 Hz, 3.6 Hz); δ3.9(m, 4H); δ4.1(m, 0.5H); δ5.0(d, J=7.5 Hz, 1H); δ7.5(br.s, 5H); δ9.5(m, 0.5H)

EXAMPLE 6

Following a procedure analogous to that of Example 1, but using 9.81 g of ethyl diethoxymethylphosphinate and 50 ml of a 2 molar solution of cyclohexylmagnesium chloride in diethyl ether and adding 20.7 g of potassium carbonate in 25 ml of water to precipitate inorganic salts, cyclohexyl(diethoxymethyl)phosphine oxide is obtained as colourless oil.

$^{31}P$ NMR 38.0 ppm (CDCl$_3$) J$_{P-H}$=455.4 Hz $^1H$ NMR δ1.3(t,J=9 Hz, 6H); δ1.8(m, 10H); δ3.9(m, 4H); δ4.8(m, 1.5H); δ5.0(d, J=8 Hz, 1H); δ9.2(m, 0.5H)

EXAMPLE 7

By a procedure analogous to that of Example 1, but using ethyl 1,1-diethoxyethylphosphinate (10.5 g) and 33.5 ml of the methylmagnesium chloride solution and adding 14.1 g of potassium carbonate in 30 ml of water to precipitate inorganic salts, methyl (1,1-diethoxyethyl) phosphine oxide is obtained as a colourless oil.

$^{31}P$ NMR 29.1 ppm (CDCl$_3$) J$_{P-H}$=463.3 Hz $^1H$ NMR δ1.4(m, 6H); δ1.6(m, 6H); δ3.8(m, 4H); δ4.5(m, 0.5H); δ9.5(m, 0.5H)

EXAMPLE 8

Ethyl diethoxymethyl phosphinate (5.0 g) is dissolved in 75 ml of dry tetrahydrofuran and this solution is cooled to an internal temperature of −40° C. under argon. To this stirred solution is added dropwise 50 ml of methyl lithium (1.0 m solution in diethyl ether) whilst maintaining the temperature below −40° C. After the addition is complete, the reaction mixture is allowed to stand at room temperature for 12 hours. 0.1 m hydrochloric acid (50 ml) is then added carefully and the mixture is extracted with dichloromethane (3×100 ml). The organic extracts are combined, dried over magnesium sulphate and evaporated under reduced pressure to remove the solvents. Distillation of the crude product obtained gives methyl(diethoxymethyl) phosphine oxide, b.p. 85°/0.02 mm identical with that obtained in Example 1.

EXAMPLE 9

Following the procedure of Example 8, but using 1.96 g of ethyl diethoxymethylphosphinate and 12.5 ml of a 1.6 molar solution of n-butyl lithium in n-hexane and adding 20 ml of 0.1M hydrochloric acid prior to extraction, n-butyl(diethoxymethyl) phosphine oxide is obtained as a colourless oil.

$^{31}P$ NMR 32.5 ppm (CDCl$_3$) J$_{P-H}$=457.1 Hz $^1H$ NMR δ1.0(m, 3H); δ1.3(t, J=9 Hz, 6H); δ-1.8 Hz(m, 6H); δ3.8(m, 4H); δ4.2(m, 0.5H); δ5.0(d, J=9 Hz, 1H); δ9.5(m, 0.5H)

EXAMPLE 10

By the procedure of Example 8, but using 30 ml of a 1.7 molar solution of tert.butyl lithium in pentane in place of the methyl lithium solution, tert.butyl(diethoxymethyl) phosphine oxide is obtained as a colourless oil.

$^{31}P$ NMR 45.9 ppm (CDCl$_3$) J$_{P-H}$=450.1 Hz $^1H$ NMR δ1.3(m, 15H); δ3.8(m, 4.5H); δ5.0(d.d, J=14.5 Hz, 3.6 Hz, 1H); δ9.0(m, 0.5 Hz)

EXAMPLE 11

Dry sodium hydride (0.42 g) is suspended in 50 ml of dry tetrahydrofuran under an argon atmosphere. To this stirred suspension is added 3.6 g (0.017 mol) of tertiary-butyl(diethoxymethyl)-phosphine oxide dissolved in 25 ml of dry tetrahydrofuran, at room temperature. Stirring is continued for 10 minutes at room temperature, during which time the solid dissolves and a gas is evolved. To the clear solution obtained is added a solution of 2.4 g (0.017 mol) of iso-butyl bromide in 25 ml of dry tetrahydrofuran. After the addition is complete, the reaction mixture is heated under reflux for 15 hours, then allowed to cool at room temperature and washed with 20 ml of water. The organic extracts are dried and evaporated under reduced pressure. The crude product is purified by chromatography on silica using ethyl acetate as eluent to give tertiary-butyl-(isobutyl)(diethoxymethyl)phosphine oxide as a colourless oil.

$^{31}$P NMR 51.6 ppm (CDCl$_3$)

$^1$H NMR δ1.3(m, 21H); δ1.6(m, 2H); δ2.2(m, 1H); δ3.8(m, 4H); δ4.8(d, J=11 Hz, 1H)

EXAMPLE 12

Tertiary-butyl(diethoxymethyl)phosphine oxide (2.5 g), (0.012 mol) is dissolved in 35 ml of dry tetrahydrofuran and cooled to −78° C. under an argon atmosphere. To this stirred solution is added 9.0 ml of n-butyl lithium (1.6M solution in hexane) and the mixture is stirred at −78° C. for 10 minutes. After this time, a solution of 2.47 g (0.014 mol) of benzyl bromide in 15 ml of dry tetrahydrofuran is added, and the reaction mixture is allowed to warm to room temperature. After stirring for 3 hours at room temperature, 10 ml of saturated ammonium chloride solution is added and the product is extracted into diethyl ether (2×100 ml). The combined organic extracts are dried and evaporated under reduced pressure to give a crude product. This is purified by chromatography on silica, using ethyl acetate as eluent, to give tertiary-butyl(benzyl)(diethoxymethyl) phosphine oxide as a colourless oil.

$^{31}$P NMR 49.5 ppm (CDCl$_3$)

$^1$H NMR δ1.3(m, 15H); δ3.2(d.d, J=9 Hz, 2H); δ3.8(m, 4H); δ4.7(d, J=9 Hz, 1H); δ7.4(m, 5H)

EXAMPLE 13

A solution of 1.2 g (0.005 mol) of tertiary-butyl(isobutyl)(diethoxymethyl) phosphine oxide in 10 ml of 5% hydrochloric acid is heated at 80° C. for 9 hours. After this the mixture is allowed to cool to room temperature, evaporated under reduced pressure and the crude product is extracted into chloroform and washed with water. The organic extract is dried and evaporated to give tertiary-butyl(iso-butyl) phosphine oxide as a pale yellow oil.

$^{31}$P NMR 48.1 ppm (CDCl$_3$) J$_{P-H}$=437.0 Hz $^1$H NMR δ2.4-1.1(m, 18H); δ4.1(br.d, J=11 Hz, 0.5H); δ9.0(br.d, J=11 Hz, 0.5H)

EXAMPLE 14

Following a procedure analogous to that to Example 13, but using tert.butyl(benzyl)(diethoxymethyl) phosphine oxide (1.7 g) and 15 ml of concentrated hydrochloric acid, tert.butyl(benzyl) phosphine oxide is obtained as a white solid, m.p. 80°-2° C.

$^{31}$P NMR 51.7 ppm (CDCl$_3$) J$_{P-H}$=450.1 Hz $^1$H NMR δ1.2(d, J=27 Hz, 9H); δ3.1(br.d, 2H); δ4.0(m, 0.5H); δ7.3(br.s, 5H); δ9.0(m, 0.5H)

EXAMPLE 15

Following the procedure of Example 1, but using ethyl magnesium bromide instead of methyl magnesium bromide and adding the bromide to the phosphinate, there is obtained ethyl(diethoxymethyl) phosphine oxide.

$^{31}$PNMR 32.6 ppm (CDCl$_3$) J$_{P-H}$=462 Hz

EXAMPLE 16

Following the procedure of Example 1, but using 10.2 ml of a molar solution of allyl magnesium bromide instead of the 3-molar solution of methyl magnesium bromide and adding the bromide to 2.0 g of the phosphinate, there is obtained allyl (diethoxymethyl) phosphine oxide.

$^{31}$PNMR 30.8 ppm (CDCl$_3$) J$_{P-H}$=460.7 Hz

EXAMPLE 17

Following a procedure analogous to that of Example 11 but using phenyl(diethoxymethyl)phosphine oxide instead of tertiary-butyl(diethoxymethyl)phosphine oxide and n-propyl bromide instead of iso-butyl bromide there is obtained phenyl(n-propyl)(diethoxymethyl)phosphine oxide as a colourless oil.

$^{31}$P NMR 35.845 ppm (CDCl$_3$)

EXAMPLE 18

Following a procedure analogous to that of Example 13 but using phenyl(n-propyl)(diethoxymethyl)phosphine oxide instead of tertiary-butyl(isobutyl)(diethoxymethyl)phosphine oxide, there is obtained phenyl (n-propyl)phosphine oxide as a colourless oil.

$^{31}$P NMR 29.956 ppm (CDCl$_3$) J$_{P-H}$477.4 Hz

EXAMPLE 19

Following a procedure analogous to that of Example 17 but using methyl iodide instead of n-propyl bromide there is obtained phenyl(methyl)(diethoxymethyl)phosphine oxide.

EXAMPLE 20

Following a procedure analogous to that of Example 18 but using phenyl(methyl)(diethoxymethyl)phosphine oxide instead of phenyl(n-propyl)(diethoxymethyl)phosphine oxide there is obtained phenyl(methyl)phosphine oxide.

EXAMPLE 21

Following a procedure analogous to that of Example 12, but using methyl(diethoxymethyl)phosphine oxide instead of tert-butyl(diethoxymethyl)phosphine oxide and using methyl iodide instead of benzyl bromide, there is obtained dimethyl(diethoxymethyl)phosphine oxide.

$^{31}$P NMR 42.9 ppm (CDCl$_3$)

EXAMPLE 22

Following a procedure analogous to that of Example 12, but using n-butyl(diethoxymethyl) phosphine oxide instead of tertiary-butyl(diethoxymethyl)phosphine oxide, there is obtained n-butyl(benzyl)(diethoxymethyl)phosphine oxide.

EXAMPLE 23

Following a procedure analogous to that of Example 14, but using n-butyl(benzyl)(diethoxymethyl)phosphine oxide instead of tertiary-butyl (benzyl)(diethoxymethyl)phosphine oxide, there is obtained n-butyl(benzyl)phosphine oxide characterised by the following $^1$H NMR resonance peaks:

$^1$H-NMR(CDCl$_3$): δ0.90 (t, 3H); δ1.4-1.7(m, 6H) δ3.1-3.4 (m, 2H); δ7.2-7.4 (m, 5H) δ6.13+δ7.66 (s, 1H).

EXAMPLE 24

To a solution of n-butyl(benzyl)phosphine oxide (13.2 g, 0.067 mol) and trimethylsilyl chloride (12.7 ml, 0.101 mol) in tetrahydrofuran (100 ml) is added triethylamine (18.7 ml, 0.134 mol) under a nitrogen atmosphere at 0°–5° C. over a period of 15 minutes. After stirring for 2 hours at 0°–5° C., 2,6-dimethoxybenzoyl chloride (13.5 g, 0.067 mol) diluted with tetrahydrofuran (50 ml) is added over a period of 20 minutes. Stirring at 0°–5° C. is continued for 2 hours, then the solution is allowed to warm to room temperature and filtered over silica gel. The resulting solution is concentrated in vacuo and the residue is recrystallized from a hexane/ethyl acetate mixture. The product is n-butyl(benzyl)(2,6-dimethoxybenzoyl)phosphine oxide having a melting point of 56°–57° C.

EXAMPLE 25

Following a procedure analogous to that of Example 24, but using 2,4,6-trimethylbenzoyl chloride instead of 2,6-dimethoxybenzoyl chloride, there is obtained n-butyl(benzyl)(2,4,6-trimethylbenzoyl)phosphine oxide as a yellow oil.

What is claimed is:

1. A process for the preparation of a phosphine oxide which comprises
   (A) reacting a phosphinate ester having a protecting group on the phosphorus atom with an organomagnesium halide or an organolithium compound at a temperature of −70° C. to 65° C. to obtain a protected primary phosphine oxide,
   (B) converting the protected primary phosphine oxide obtained into a protected secondary phosphine oxide by reaction either
   (a) with a compound of formula VI $$R^6Z \qquad \qquad VI$$

where $R^6$ denotes a monovalent organic group which is a $C_1-C_{20}$ aliphatic group, a $C_3-C_{12}$ cycloaliphatic group, a $C_6-C_{15}$ aromatic group or a $C_7-C_{16}$ araliphatic group, or
   (b) with a silylating agent of formula VII $$(R^7)_3SiX \qquad \qquad VII$$

in the presence of a tertiary base, followed by reaction of the silyl compound obtained with a compound of formula VI, $$R^6Z \qquad \qquad VI$$

where $R^6$ is as defined above, each $R^7$ independently denotes a $C_1-C_6$ alkyl group, X denotes chlorine, bromine or iodine and Z denotes a leaving atom or group, and
   (C) removing a protecting group from the protected secondary phosphine oxide by treatment with (i) an acid under hydrolytic conditions or (ii) an organic silyl halide followed by hydrolysis.

2. A process according to claim 1, in which the phosphinate ester is of formula

where $R^1$ denotes a $C_1-C_4$ alkyl group and Q denotes a protecting group, the organomagnesium halide is of formula $$R^5MgX \qquad \qquad III$$

and the organolithium compound is of formula $$R^5Li \qquad \qquad IV$$

where $R^5$ denotes a monovalent organic group which is a $C_1-C_{20}$ aliphatic group, a $C_3-C_{12}$ cycloaliphatic group, a $C_6-C_{15}$ aromatic group or a $C_7-C_{16}$ araliphatic group, and X denotes a chlorine, bromine or iodine atom.

3. A process according to claim 2, in which Q denotes a group of formula

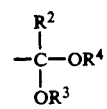

where $R^2$ denotes a hydrogen atom or a $C_1-C_4$ alkyl group and $R^3$ and $R^4$ each independently denote a $C_1-C_4$ alkyl group.

4. A process according to claim 3, in which $R^2$ denotes a hydrogen atom or methyl and $R^3$ and $R^4$ each denote ethyl.

5. A process according to claim 2, in which $R^5$ denotes a $C_1-C_{20}$ alkyl group, a $C_2-C_{20}$ alkenyl group, a $C_3-C_{12}$ cycloalkyl group, a $C_6-C_{15}$ aryl group optionally substituted by halogen, or a $C_7-C_{16}$ aralkyl group.

6. A process according to claim 5, in which $R^5$ denotes a $C_1-C_{18}$ alkyl group, a $C_2-C_{12}$ alkenyl group, a $C_3-C_8$ cycloalkyl group, a $C_6-C_{10}$ aryl group optionally substituted by halogen, or a $C_7-C_{11}$ aralkyl group.

7. A process according to claim 6, in which $R^5$ denotes methyl, ethyl, n-butyl, tert.butyl, octadecyl, allyl, cyclohexyl, phenyl, p-chlorophenyl or benzyl.

8. A process according to claim 2, in which $R^5$ is not allyl and the organomagnesium halide or organolithium compound is used in an amount of at least 2 mols per mol of the phosphinate ester.

9. A process according to claim 2, in which $R^5$ is allyl and the organomagnesium halide or organolithium compound is used in an amount of 1 mol or less per mol of the phosphinate ester.

10. A process according to claim 1, in which the phosphinate ester is reacted with the organomagnesium halide at 0° to 25° C.

11. A process according to claim 1, in which the phosphinate ester is reacted with the organolithium compound at −50° C. to 25° C.

12. A process according to claim 1, in which $R^6$ denotes a $C_1-C_4$ alkyl group or a $C_7-C_9$ aralkyl group.

13. A process according to claim 12, in which $R^6$ denotes methyl, n-propyl, isobutyl or benzyl.

* * * * *